(12) United States Patent
Harada et al.

(10) Patent No.: US 8,902,515 B2
(45) Date of Patent: Dec. 2, 2014

(54) OBJECTIVE OPTICAL SYSTEM AND ENDOSCOPE USING SAME

(71) Applicant: FUJIFILM Corporation, Tokyo (JP)

(72) Inventors: Keisuke Harada, Saitama-ken (JP); Yoshiaki Ishii, Saitama-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/266,139

(22) Filed: Apr. 30, 2014

(65) Prior Publication Data
US 2014/0233114 A1 Aug. 21, 2014

Related U.S. Application Data

(63) Continuation of application No. PCT/JP2012/006972, filed on Oct. 31, 2012.

(30) Foreign Application Priority Data

Nov. 1, 2011 (JP) ................. 2011-240150

(51) Int. Cl.
*G02B 23/24* (2006.01)
*G02B 9/34* (2006.01)
*H04N 5/225* (2006.01)
*G02B 13/04* (2006.01)
*A61B 1/00* (2006.01)

(52) U.S. Cl.
CPC ............ *G02B 23/243* (2013.01); *A61B 1/0096* (2013.01); *G02B 13/04* (2013.01); *A61B 1/00188* (2013.01); *G02B 9/34* (2013.01)
USPC .......................................... 359/753; 348/345

(58) Field of Classification Search
CPC ........ G02B 23/243; G02B 9/34; G02B 13/04; A61B 1/00096; A61B 1/00188; H04N 2005/2255; H04N 5/225
USPC ........... 348/345; 359/660, 749, 752, 753, 781
See application file for complete search history.

(56) References Cited

U.S. PATENT DOCUMENTS

| 4,986,642 A | 1/1991 | Yokota et al. |
| 2009/0086017 A1 | 4/2009 | Miyano |
| 2010/0305405 A1 | 12/2010 | Miyano |
| 2014/0233112 A1* | 8/2014 | Harada .................... 359/781 |
| 2014/0233113 A1* | 8/2014 | Harada et al. ............. 359/781 |

FOREIGN PATENT DOCUMENTS

| JP | 63-261213 | 10/1988 |
| JP | 01-134324 | 5/1989 |

(Continued)

OTHER PUBLICATIONS

International Search Report, PCT/JP2012/006972, Jan. 15, 2013.

*Primary Examiner* — David N Spector
(74) *Attorney, Agent, or Firm* — Young & Thompson

(57) ABSTRACT

An objective optical system includes: a first lens group having a negative power; an aperture stop; and a second lens group having a positive power, provided in this order from an object side. The first lens group includes a first lens, which is a negative single lens, and a cemented lens formed by a positive lens and a negative lens, provided in this order from the object side. The second lens group includes a fourth lens, which is a positive single lens, and a cemented lens formed by a positive lens and a negative lens, provided in this order from the object side. The objective optical system simultaneously satisfies Conditional Formulae (1) $-1.5 < f123/f < -0.5$ and (2) $1.8 < f456/f < 2.1$, wherein f is the focal length of the entire system, f123 is the combined focal system of the first lens group, and f456 is the combined focal length of the second lens group.

19 Claims, 13 Drawing Sheets

EXAMPLE 1

(56) References Cited

FOREIGN PATENT DOCUMENTS

| | | |
|---|---|---|
| JP | 10-111454 | 4/1998 |
| JP | 2004-145256 | 5/2004 |
| JP | 2004-205779 | 7/2004 |
| JP | 2006-243092 | 9/2006 |
| JP | 2008-257108 | 10/2008 |
| JP | 2008-257109 | 10/2008 |
| JP | 2009-080413 | 4/2009 |
| JP | 2010-276923 | 12/2010 |
| JP | 2011-145315 | 7/2011 |
| WO | WO 2012/0008312 | 1/2012 |

* cited by examiner

EXAMPLE 1

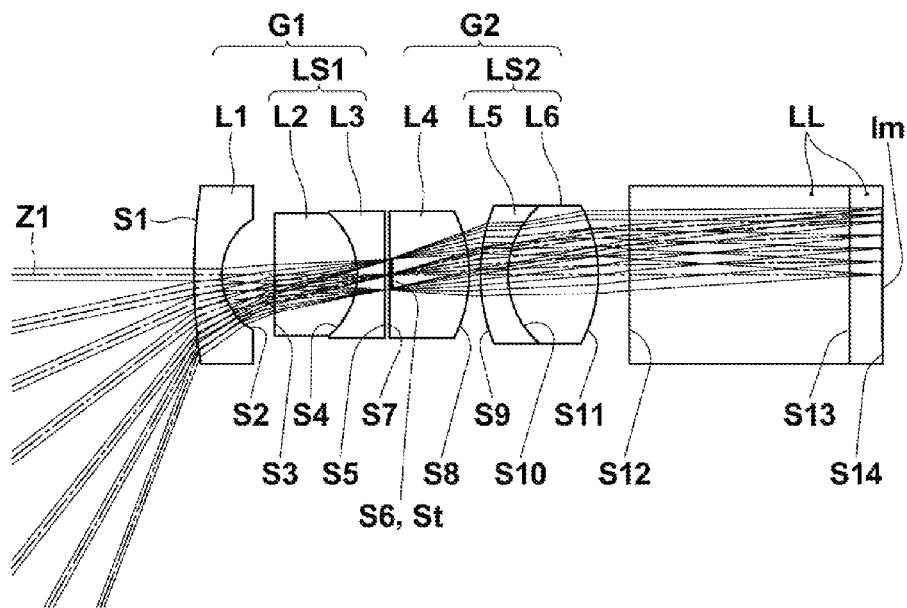
FIG.3  EXAMPLE 2
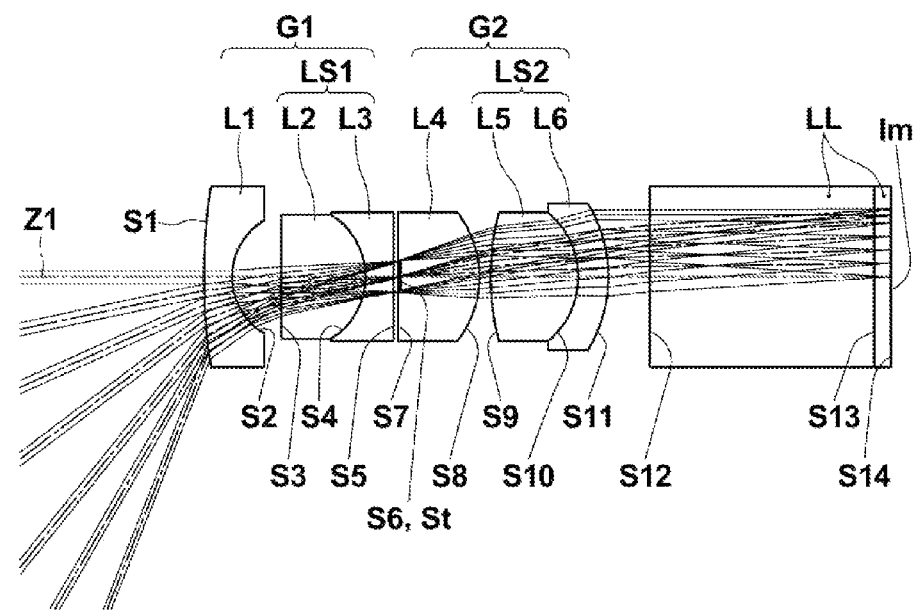
FIG.4  EXAMPLE 3

FIG.5  EXAMPLE 4
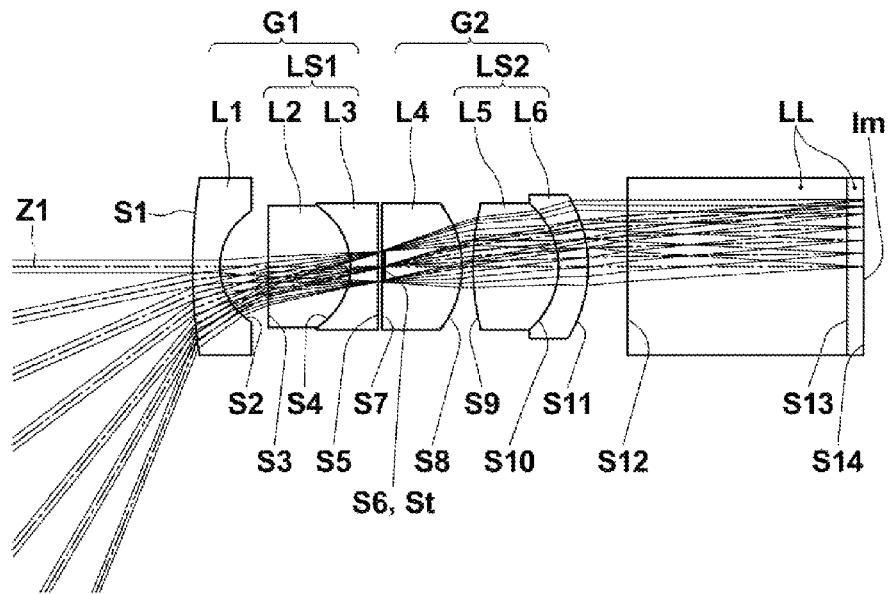
FIG.6  EXAMPLE 5
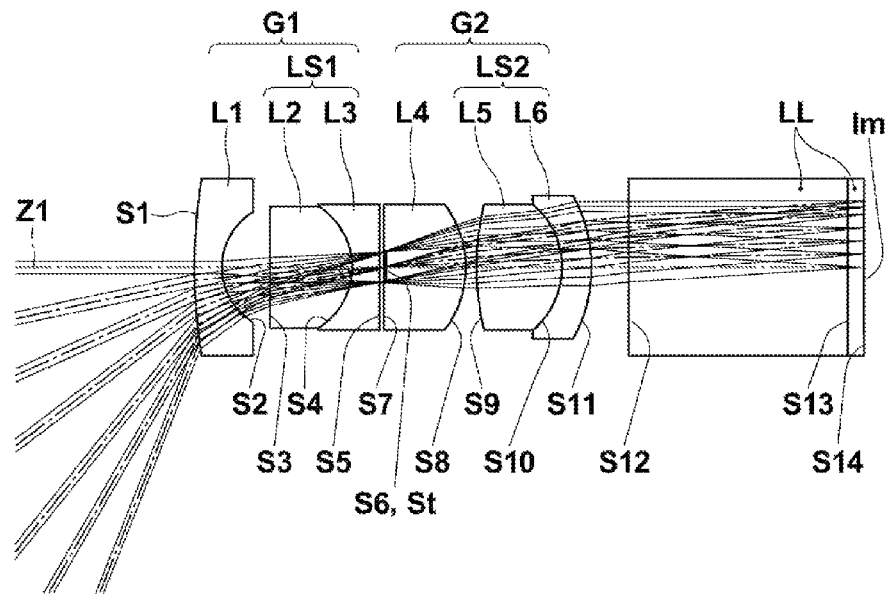

FIG.7  EXAMPLE 6
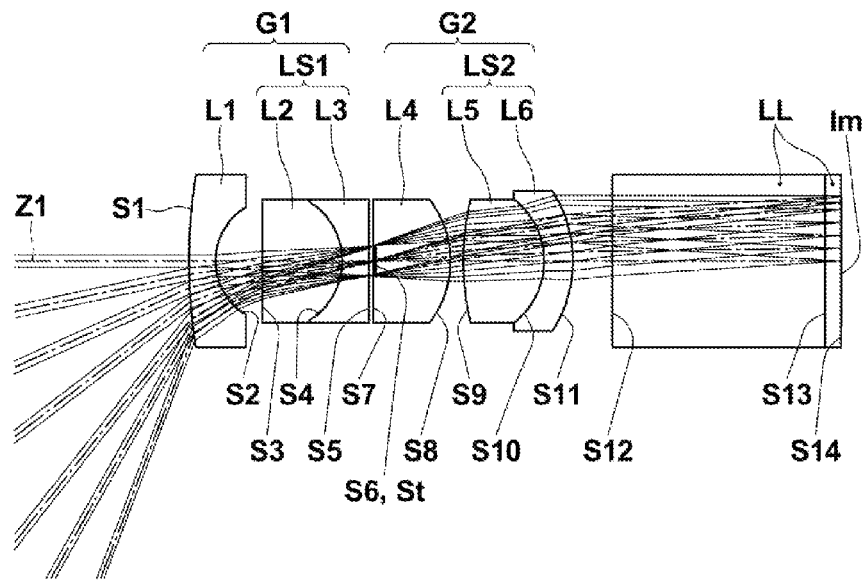
FIG.8  EXAMPLE 7
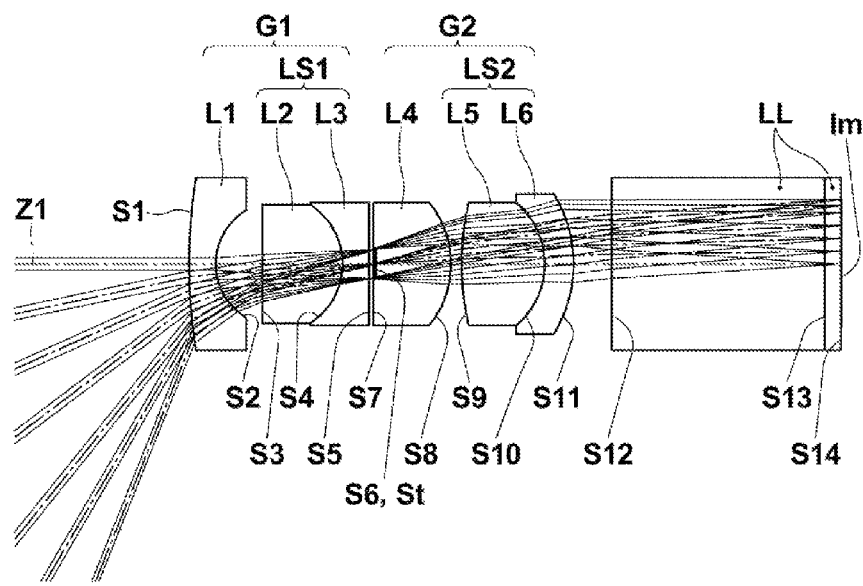

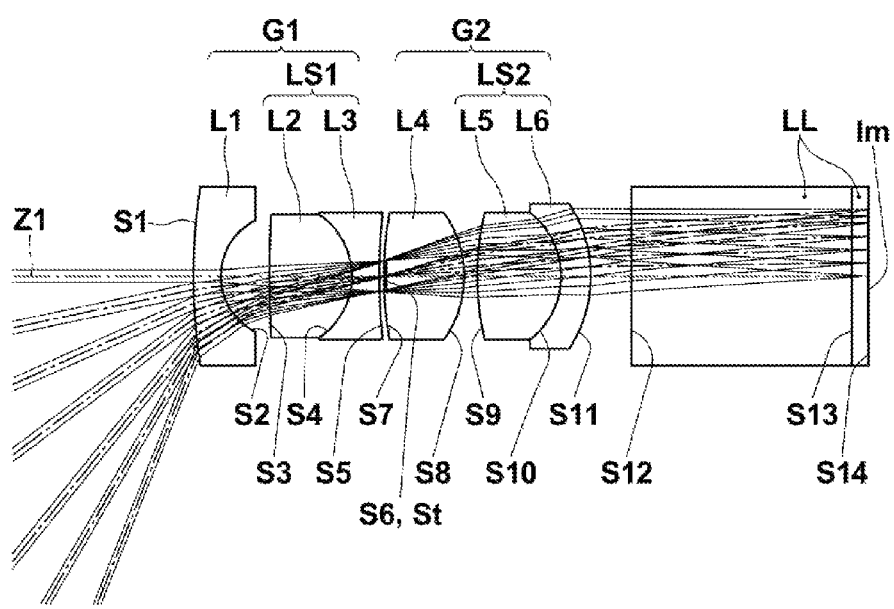
FIG.9 EXAMPLE 8

FIG.12
EXAMPLE 3
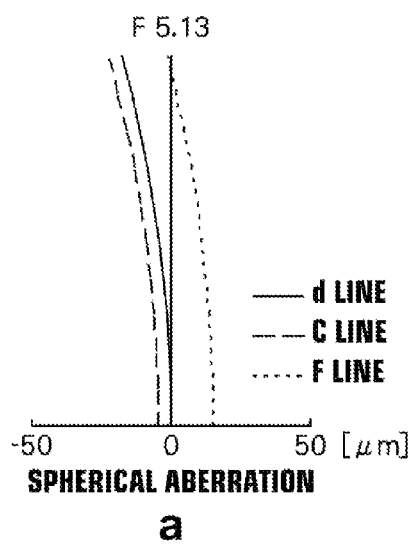
a  SPHERICAL ABERRATION
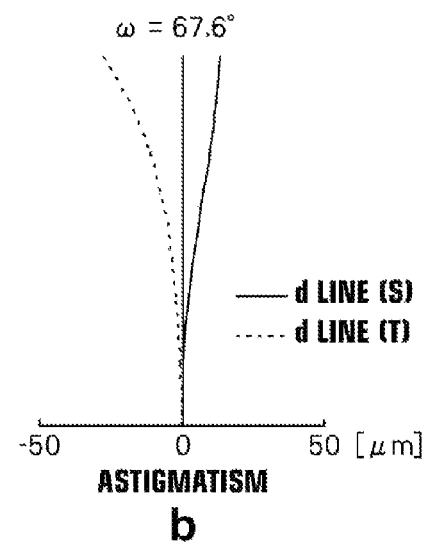
b  ASTIGMATISM
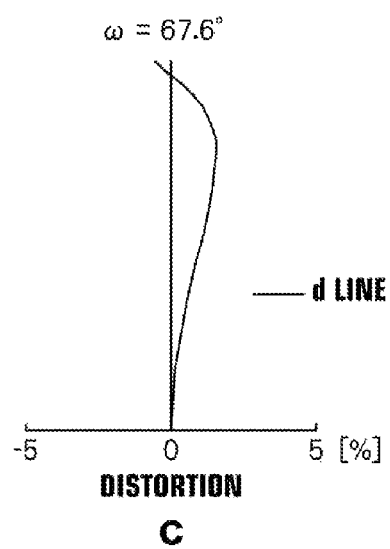
c  DISTORTION
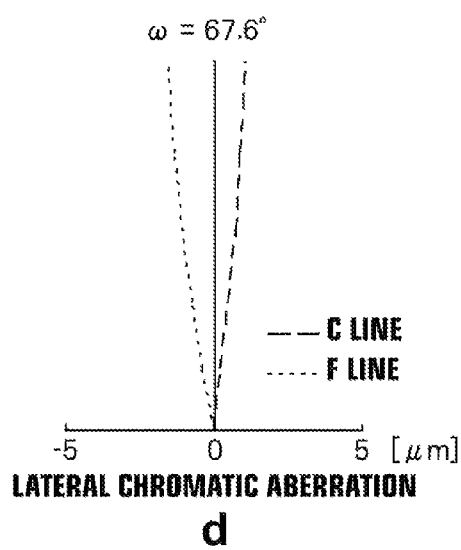
d  LATERAL CHROMATIC ABERRATION

FIG.13
EXAMPLE 4
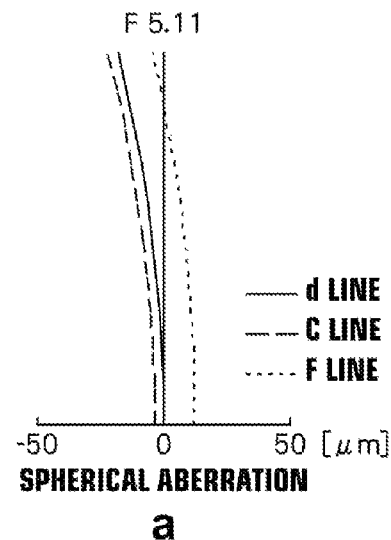
a SPHERICAL ABERRATION
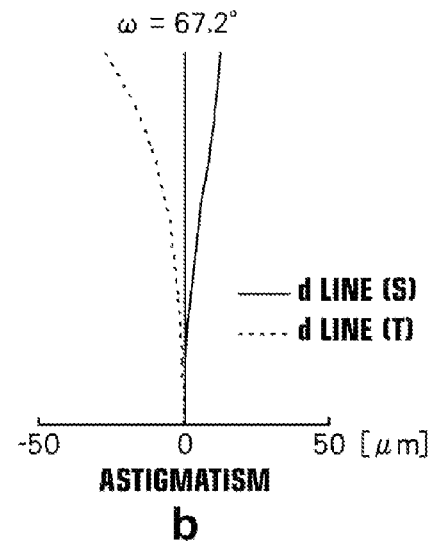
b ASTIGMATISM
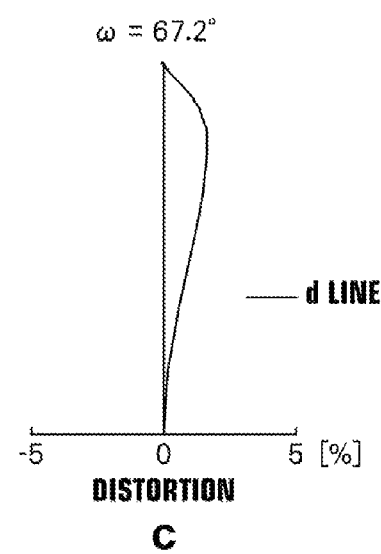
c DISTORTION
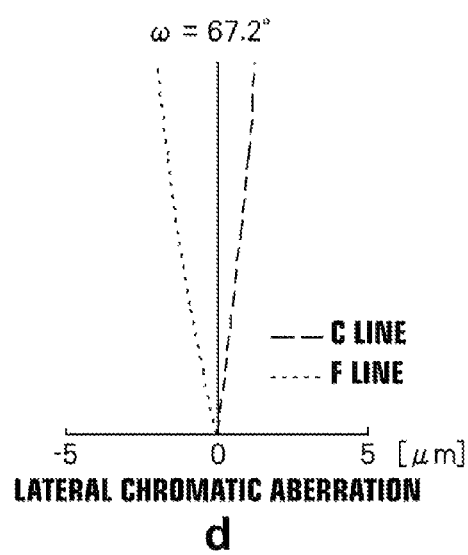
d LATERAL CHROMATIC ABERRATION

FIG.15
EXAMPLE 6
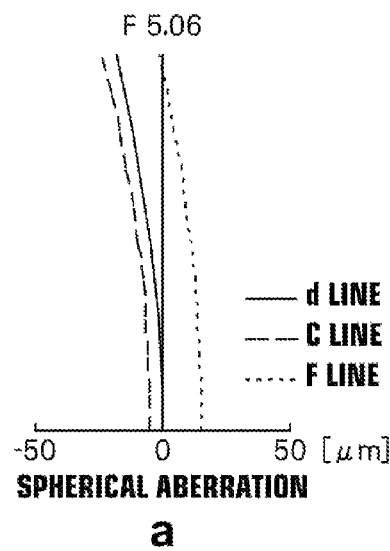
a
SPHERICAL ABERRATION
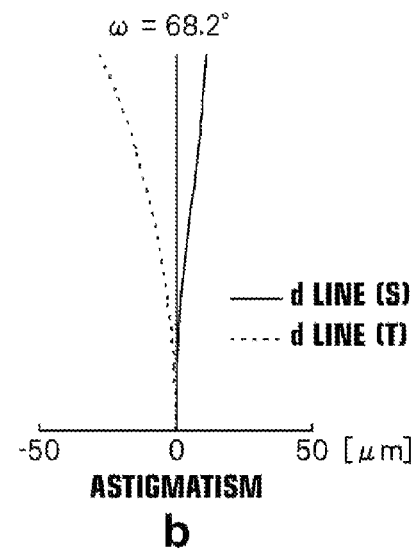
b
ASTIGMATISM
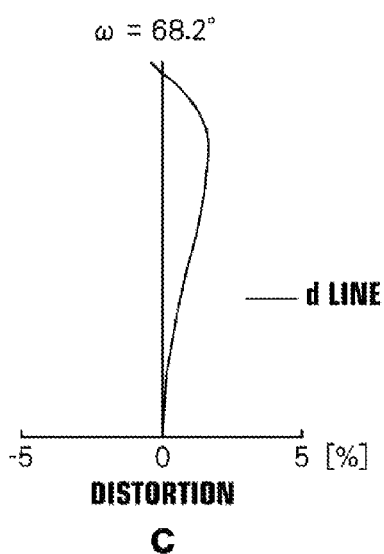
c
DISTORTION
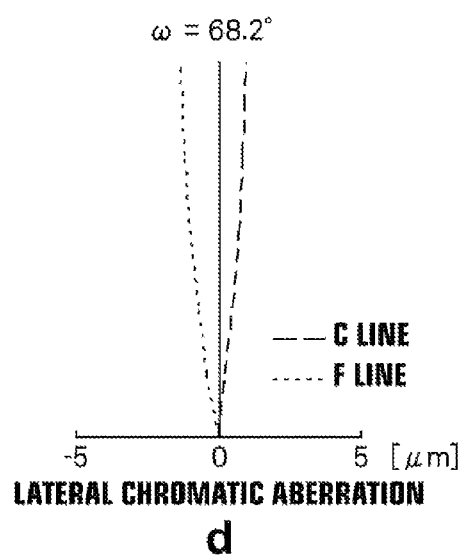
d
LATERAL CHROMATIC ABERRATION

FIG.16
EXAMPLE 7
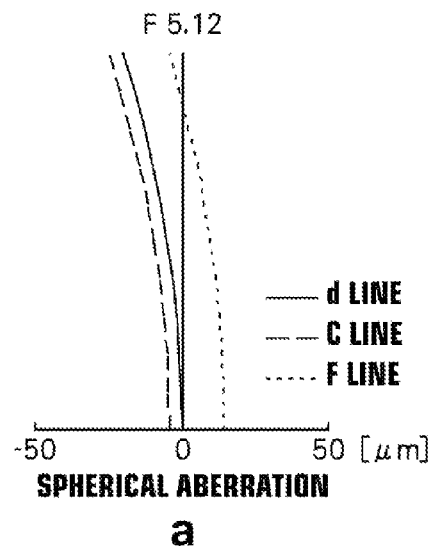
a SPHERICAL ABERRATION
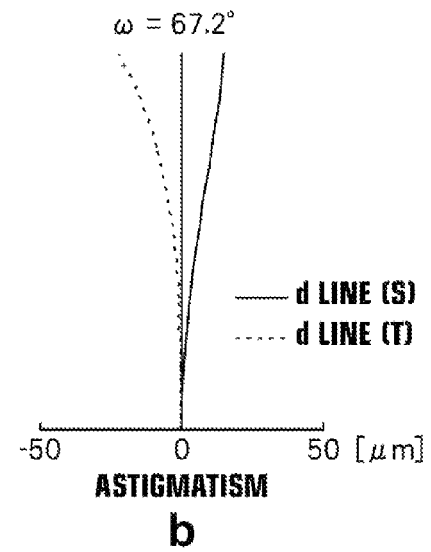
b ASTIGMATISM
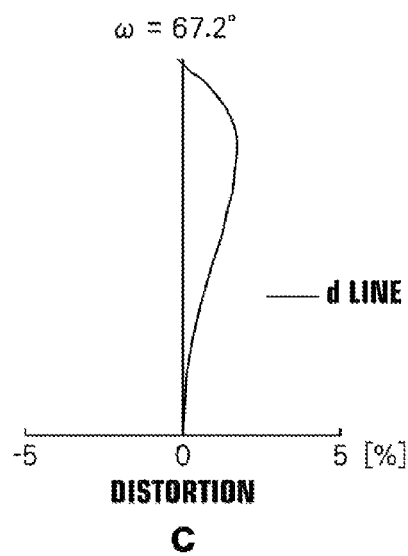
c DISTORTION
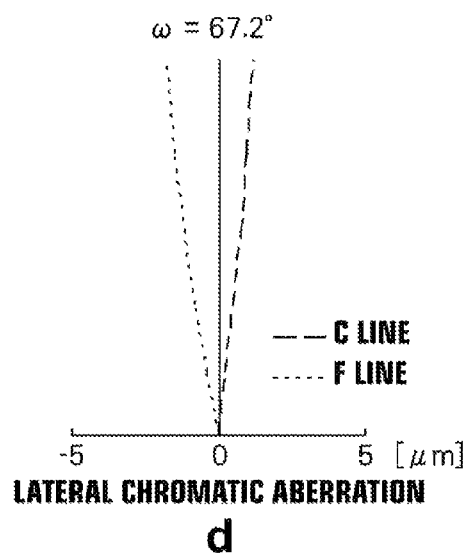
d LATERAL CHROMATIC ABERRATION

OBJECTIVE OPTICAL SYSTEM AND ENDOSCOPE USING SAME

TECHNICAL FIELD

The present invention is related to an objective optical system having a first lens group and a second lens group, with an aperture stop interposed therebetween. The present invention is also related to an endoscope that employs such an objective optical system.

DESCRIPTION OF THE RELATED ART

Accompanying increases in the density of recent imaging devices, the sizes of light receiving sizes of the imaging devices are becoming smaller. For example, objective optical systems having wide angles of view that focus optical images that represent subjects onto small light receiving surfaces are used in endoscopes. Here, the angle of view will become narrow, if the size of an optical image is to be decreased while maintaining the back focus of an objective optical system constant, that is, without changing the size of a space in which an optical path converting prism and the like are to be inserted. For this reason, there are known objective optical systems for endoscopes that realize widening of the angle of view, by adopting a retro focus type optical system and by decreasing the radius of curvature of an image side lens surface of a negative lens provided most toward the object side (refer to Japanese Unexamined Patent Publication Nos. 2008-257108, 2008-257109, and 2004-205779). Note that the expression "negative lens" refers to a lens having a negative refractive power. In addition, the expression "image side lens surface" refers to a lens surface of a lens toward the image side.

DISCLOSURE OF THE INVENTION

As described above, it is possible to widen the angle of view by decreasing the radius of curvature of an image side surface of a negative lens provided most toward the object side. However, there is a tendency for field curvature to be overcorrected (corrected excessively) as the radius of curvature is decreased. Imparting a positive refractive power to a cemented lens provided more toward the object side than an aperture stop is a known technique for correcting field curvature.

However, if such a configuration is adopted, the burden surface of widening the angle of view is concentrated on a single lens (the image side surface of the negative lens provided most toward the object side). If even a small amount of tilt or eccentricity occurs in this lens surface, the size of the angle of view will change significantly or aberrations will increase significantly. Therefore, an objective optical system which is actually manufactured may not achieve a predetermined optical performance, that is, a predetermined angle of view, or a great amount of distortion and field curvature may be generated.

For this reason, there is demand for an objective optical system in which the burden surface of widening the angle of view is not concentrated on a single lens.

The present invention has been developed in view of the foregoing circumstances. It is an object of the present invention to provide an objective optical system in which the angle of view is widened while suppressing variations in angles of view and the generation of aberrations caused by tilting and eccentricities of a lens surface caused due to circumstances during production related to a first lens group in front of an aperture stop. It is another object of the present invention to provide an endoscope that employs such an objective optical system.

An objective optical system of the present invention comprises:
a first lens group having a negative refractive power;
an aperture stop; and
a second lens group having a positive refractive power, provided in this order from an object side;
the first lens group comprising a negative single lens and a cemented lens having a negative refractive power, formed by cementing a positive lens and a negative lens together, provided in this order from the object side;
the second lens group comprising a positive single lens and a cemented lens having a positive refractive power, formed by cementing a positive lens and a negative lens together, provided in this order from the object side; and
the objective optical system simultaneously satisfying Conditional Formulae (1) and (2) below:

$$-1.5 < f123/f < -0.5 \tag{1}$$

$$1.8 < f456/f < 2.1 \tag{2}$$

wherein f is the combined focal length of the entire lens system, f123 is the combined focal length of the first lens group, and f456 is the combined focal length of the second lens group.

It is desirable for the objective optical system to satisfy Conditional Formula (1a): $-1.4 < f123/f < -0.6$, and more desirable for the objective optical system to satisfy Conditional Formula (1b): $-1.3 < f123/f < -0.7$.

It is desirable for the objective optical system to satisfy Conditional Formula (2a): $1.84 < f456/f < 2.1$, and more desirable for the objective optical system to satisfy Conditional Formula (2b): $1.86 < f456/f < 2.0$.

The cemented lens within the first lens group of the objective optical system may be formed by a positive lens having a convex surface toward the image side, and a negative lens, provided in this order from the object side.

The cemented lens within the second lens group of the objective optical system may be formed by a positive lens and a negative meniscus lens having a convex surface toward the image side, provided in this order from the object side. Alternatively, the cemented lens within the second lens group may be formed by a negative lens and a positive lens having a convex surface toward the image side, provided in this order from the object side.

It is desirable for the objective optical system to satisfy Conditional Formula (3): $f1/f < -1.1$, more desirable for the objective optical system of the present invention to satisfy Conditional Formula (3a): $-1.5 < f1/f < -1.1$, and even more desirable for the objective optical system of the present invention to satisfy Conditional Formula (3b): $-1.4 < f1/f < -1.2$.

Here, f1 is the focal length of the lens provided most toward the object side, and f is the focal length of the entire lens system.

It is desirable for the objective optical system to satisfy Conditional Formula (4): $1.92 < f2-6/f < 3$, more desirable for the objective optical system of the present invention to satisfy Conditional Formula (4a): $1.92 < f2-6/f < 2.5$, and even more desirable for the objective optical system of the present invention to satisfy Conditional Formula (4b): $1.92 < f2-6/f < 2.2$.

Here, f2-6 is the combined focal length of the lenses other than the lens provided most toward the object side, and f is the focal length of the entire lens system.

The objective optical system may be employed as the objective optical system of an endoscope.

An endoscope of the present invention is equipped with the objective optical system of the present invention.

The objective optical system of the present invention substantially consists of two lens groups. Note that the expression "substantially consists of two lens groups" refers to cases including those in which the objective optical systems also include other components, such as lenses that practically do not have any power, optical elements other than lenses such as aperture stops and cover glasses, and mechanical components such as lens flanges, a lens barrel, an imaging device, and a blur correcting mechanism.

The objective optical system of the present invention substantially consists of six lenses. Note that the expression "substantially consists of six lenses" refers to cases including those in which the objective optical systems also include other components, such as lenses that practically do not have any power, optical elements other than lenses such as aperture stops and cover glasses, and mechanical components such as lens flanges, a lens barrel, an imaging device, and a blur correcting mechanism.

As described above, the objective optical system may be constituted only by two lens groups and six lenses. Alternatively, the objective optical system may also include lenses that practically do not have any power and optical elements other than lenses, in addition to the two lens groups and the six lenses.

Note that with respect to the number of lenses in cases that cemented lenses are included, cemented lenses formed by cementing n lenses together will be counted as n lenses.

A single lens refers to one lens. That is, the expression "single lens" refers to an individual lens which is not cemented to another lens.

In the case that aspherical surfaces are employed in the objective optical system, the convexities and concavities of the aspherical surfaces, the signs of refractive powers, and the radii of curvature of the aspherical surfaces will be defined as those in the paraxial regions thereof.

Note that the expression "negative lens" refers to a lens having a negative refractive power, and the expression "positive lens" refers to a lens having a positive refractive power. In addition, the expression "image side lens surface" refers to a lens surface of a lens toward the image side.

In the objective optical system of the present invention and the endoscope that employs this objective optical system, the first lens group having the negative refractive power, the aperture stop, and the second lens group having the positive refractive power are provided in this order from the object side. The first lens group is provided with the negative single lens and the cemented lens having a negative refractive power, formed by cementing the positive lens and the negative lens together, in this order from the object side. The second lens group is provided with the positive single lens and the cemented lens having a positive refractive power, formed by cementing the positive lens and the negative lens together, in this order from the object side. The constituent element that bears the burden of widening the angle of view is mainly the lens provided most toward the object side. However, by imparting the cemented lens in front of the aperture stop with a negative refractive power, the burden of widening the angle of view was distributed between the most object side lens and the cemented lens in front of the aperture stop. Further, the objective optical system is configured to satisfy Conditional Formula (1): $-1.5 < f123/f < -0.5$. Thereby, a balance between correction of field curvature and widening of the angle of view is achieved in the first lens group. Correction by the first lens group results in the back focus becoming shorter. Therefore, the focal length of the second lens group is adjusted by configuring the objective optical system to satisfy Conditional Formula (2): $1.8 < f456/f < 2.1$ in order to correct the back focus. The angle of view can be widened while suppressing variations in angles of view and the generation of aberrations caused by tilting and eccentricities of a lens surface caused due to circumstances during production related to a first lens group in front of an aperture stop, by the objective optical system simultaneously satisfying Conditional Formulae (1) and (2).

That is, the burden of widening the angle of view is distributed among a plurality of lens surfaces provided more toward the object side than the aperture stop, by configuring the objection optical system in the manner described above. Therefore, even if tilting or an eccentricity is present in a single lens surface, the size of the angle of view will not change significantly. In addition, even in the case that tilting or eccentricities are present in each of the plurality of lens surfaces, such tilting and eccentricities generally occur randomly. Therefore, changes in the angle of view caused by tilting and eccentricities in each of the lens surfaces cancel each other out, and changes in the angle of view of the objective optical system can be suppressed.

In addition, the range of adjustment of the focal length of the first lens group can be determined by configuring the objective optical system to satisfy Conditional Formula (1). The angle of view can be increased while maintaining the amounts of distortion and field curvature small, by adjusting the focal length of the first lens group within this range.

If the objective optical system is configured such that the value of $f123/f$ is greater than the upper limit defined in Conditional Formula (1), distortion will increase, field curvature will be generated, and an imaging surface will tilt toward an upper (excessively corrected) side. Meanwhile, if the objective optical system is configured such that the value of $f123/f$ is less than the lower limit defined in Conditional Formula (1), the angle of view will become small, the back focus will become short, and the imaging surface will tilt toward a lower (insufficiently corrected) side.

Further, the range of adjustment of the focal length of the second lens group can be determined by configuring the objective optical system to satisfy Conditional Formula (2). The back focus, which tends to become short when widening the angle of view, can be lengthened by adjusting the focal length of the second lens group within this range.

If the value of $f456/f$ is greater than the upper limit defined in Conditional Formula (2), the angle of view will become small. Meanwhile, if the value of $f456/f$ is less than the lower limit defined in Conditional Formula (2), the back focus will become short.

BRIEF DESCRIPTION OF THE DRAWINGS

FIG. 3 is a sectional diagram that illustrates the schematic configuration of an objective optical system of Example 2 along with the paths of light rays.

FIG. 4 is a sectional diagram that illustrates the schematic configuration of an objective optical system of Example 3 along with the paths of light rays.

FIG. 5 is a sectional diagram that illustrates the schematic configuration of an objective optical system of Example 4 along with the paths of light rays.

FIG. 6 is a sectional diagram that illustrates the schematic configuration of an objective optical system of Example 5 along with the paths of light rays.

FIG. 7 is a sectional diagram that illustrates the schematic configuration of an objective optical system of Example 6 along with the paths of light rays.

FIG. 8 is a sectional diagram that illustrates the schematic configuration of an objective optical system of Example 7 along with the paths of light rays.

FIG. 9 is a sectional diagram that illustrates the schematic configuration of an objective optical system of Example 8 along with the paths of light rays.

FIG. 12 is collection of diagrams that illustrate aberrations of the objective optical system of Example 3.

FIG. 13 is collection of diagrams that illustrate aberrations of the objective optical system of Example 4.

FIG. 15 is collection of diagrams that illustrate aberrations of the objective optical system of Example 6.

FIG. 16 is collection of diagrams that illustrate aberrations of the objective optical system of Example 7.

BEST MODE FOR CARRYING OUT THE INVENTION

Hereinafter, objective optical systems of the present invention and endoscopes that employ the objective optical systems will be described with reference to the attached drawings.

Figure 1:
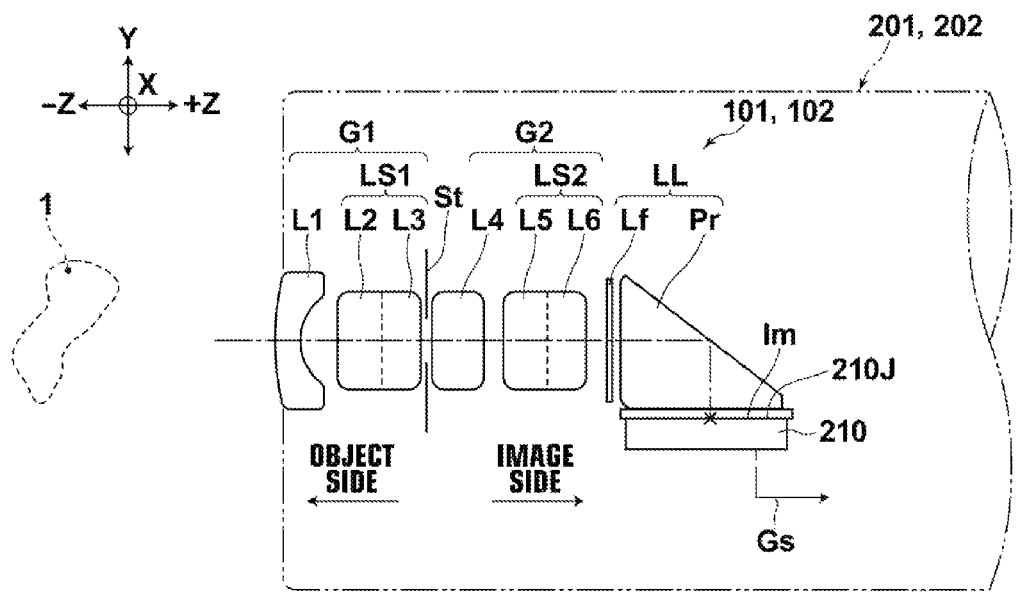
FIG. 1 is a sectional diagram that schematically illustrates the configuration of an endoscope equipped with an objective optical system according to an embodiment of the present invention.

FIG. 1 is a sectional diagram that schematically illustrates the configuration of an endoscope equipped with an objective optical system according to an embodiment of the present invention. Note that arrows X, Y, and Z in FIG. 1 indicate three directions which are perpendicular to each other, and the arrow Z indicates the same direction as that of an optical axis Z1. Note that the optical axis Z1 is an axis that matches a straight line that passes through the center of curvature of the surfaces of each of the lenses that constitute the objective optical system.

An endoscope 201 illustrated in FIG. 1 is equipped with an imaging device 210, which is a solid state imaging device such as a CCD and a CMOS, and an objective optical system 101. Note that FIG. 1 illustrates the distal end of a portion of the endoscope 201 to be inserted into a body cavity.

Light that propagates along the optical axis Z1, which is determined with respect to the single focus objective optical system 101, is deflected 90 degrees in a direction toward the imaging device 210 by an optical path converting prism Pr. A light receiving surface 210J of the imaging device 210 is provided parallel with respect to the optical axis Z1.

The imaging device 210 converts an optical image Im that represents a subject 1, which passes through the single focus objective optical system 101 and is focused on the light receiving surface 210J, into electrical signals, and outputs image signals Gs that represent the optical image Im.

The objective optical system 101 is constituted by a first lens group G1 having a negative refractive power, an aperture stop St, and a second lens group G2 having a positive refractive power, in this order from the object side (the side of the −Z direction in FIG. 1). The first lens group G1 is provided with a first lens L1, which is a single lens having a negative refractive power, and a cemented lens LS1 having a negative refractive power as a whole, formed by cementing a lens having a positive refractive power and a lens having a negative refractive power together, in this order from the object side. The second lens group G2 is provided with a fourth lens L4, which is a single lens having a positive refractive power, and a cemented lens LS2 having a positive refractive power as a whole, formed by cementing a lens having a positive refractive power and a lens having a negative refractive power together, in this order from the object side.

Note that the objective optical system 101 of the first embodiment is configured to satisfy Conditional Formulae (1): $-1.5<f123/f<-0.5$ and (2): $1.80<f456/f<2.1$, in addition to having the configuration described above. Here, f is the focal length of the entire lens system, f123 is the combined focal length of the first lens group, and f456 is the combined focal length of the second lens group.

Note that the objective optical system 101 is not limited to use in endoscopes, and may be employed as an objective lens in other apparatuses.

It is desirable for the objective optical system 101 to satisfy Conditional Formula (1a): $-1.4<f123/f<-0.6$, and more desirable for the objective optical system 101 to satisfy Conditional Formula (1b): $-1.3<f123/f<-0.7$. Similarly, it is desirable for the objective optical system 101 to satisfy Conditional Formula (2a): $1.84<f456/f<2.1$, and more desirable for the objective optical system 101 to satisfy Conditional Formula (2b): $1.86<f456/f<2.0$.

The operative effects of Conditional Formulae (1a) and (1b) are the same as those described above with respect to Conditional Formula (1). In addition, the operative effects of Conditional Formulae (2a) and (2b) are the same as those described above with respect to Conditional Formula (2).

In the objective optical system 101, the cemented lens LS1 within the first lens group may be constituted by a second lens L2 having a positive refractive power and a convex surface toward the image side (the +z direction in FIG. 1) and a third lens L3 having a negative refractive power, provided in this order from the object side. In the case that the second lens L2 has a convex surface toward the image side and a positive refractive power, the back focus will be sufficiently long. Thereby, insertion of optical elements LL having no power, such as the optical path converting prism Pr and a filter Lf into the optical path corresponding to the back focus will be facilitated.

In addition, in the objective optical system 101, the cemented lens LS2 within the second lens group G2 may be formed by a fifth lens L5 having a positive refractive power and a sixth lens L6, which is a meniscus lens having a negative refractive power and a convex surface toward the image side, provided in this order from the object side. By configuring the cemented lens LS2 in this manner, favorable telecentric properties can be obtained, and principal rays of light can be caused to enter the light receiving surface 210J of the imaging device 210 substantially perpendicularly.

Alternatively, in the objective optical system 101, the cemented lens LS2 within the second lens group G2 may be formed by a fifth lens L5 having a negative refractive power and a sixth lens L6 having a positive refractive power and a convex surface toward the image side, provided in this order from the object side. By configuring the cemented lens LS2 in this manner, favorable telecentric properties can be obtained as in the case described above, and principal rays of light can be caused to enter the light receiving surface 210J of the imaging device 210 substantially perpendicularly.

In addition, it is desirable for the objective optical system 101 to satisfy Conditional Formula (3): f1/f<−1.1, more desirable for the objective optical system 101 to satisfy Conditional Formula (3a): −1.5<f1/f<−1.1, and even more desirable for the objective optical system 101 to satisfy Conditional Formula (3b): −1.4<f1/f<−1.2. Here, f1 is the focal length of the lens provided most toward the object side, and f is the focal length of the entire lens system.

Widening of the angle of view to a range from 130 degrees to 140 degrees will become possible if Conditional Formula (3) is satisfied.

Here, if the value of f1/f is greater than the upper limit defined in Conditional Formula (3), the heights of rays of light that pass through the first lens L1 will become high, although the angle of view can be increased. Therefore, it will become necessary to increase the outer diameter of the first lens L1. Meanwhile, if the value of f1/f is less than the lower limit defined in Conditional Formula (3), the angle of view will decrease, and it will become difficult to achieve a desired widening of the angle of view in the objective optical system 101. Note that the operational effects of Conditional Formulae (3a) and (3b) are the same as those described above.

In addition, it is desirable for the objective optical system 101 to satisfy Conditional Formula (4): 1.92<f2−6/f<3, more desirable for the objective optical system 100 to satisfy Conditional Formula (4a): 1.92<f2−6/f<2.5, and even more desirable for the objective optical system 100 to satisfy Conditional Formula (4b): 1.92<f2−6/f<2.2. Here, f2−6 is the combined focal length of the lenses other than the first lens L1 provided most toward the object side, and f is the focal length of the entire lens system. That is, f2−6 is the combined focal length of the second lens L2, the third lens L3, the fourth lens L4, the fifth lens L5, and the sixth lens L6.

If the value of f2−6/f is greater than the upper limit defined in Conditional Formula (4), the angle of view will become small, and it will become difficult to achieve a widening of the angle of view desired for the objective optical system 101. Meanwhile, if the value of f2−6/f is less than the lower limit defined in Conditional Formula (4), the back focus will become short, and insertion of optical elements LL having no power, (for example, the optical path converting prism Pr and the filter Lf) into the optical path corresponding to the back focus will become difficult. Note that the operational effects of Conditional Formulae (4a) and (4b) are the same as those described above.

EXAMPLES

Next, Examples 1 through 8, which indicate data of specific numerical values of the objective optical system of the present invention, will be described with reference to FIGS. 2 through 9, FIGS. 10 through 17, Tables 1 through 8, and Table 9. Note that reference numerals within FIGS. 2 through 9 that match the reference numerals in FIG. 1 that illustrates the objective optical system 101 indicate corresponding constituent elements.

Example 1

Figure 2:
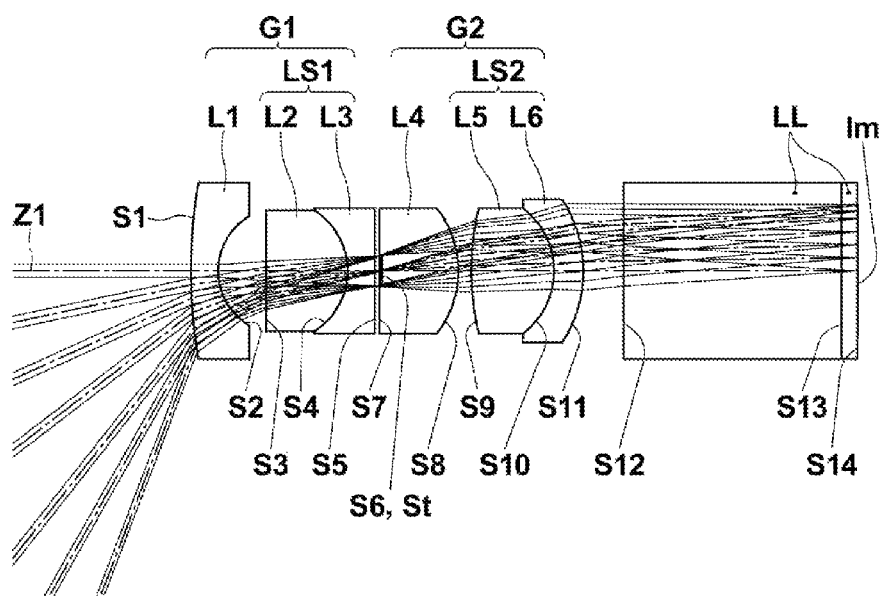
FIG. 2 is a sectional diagram that illustrates the schematic configuration of an objective optical system of Example 1 along with the paths of light rays.

FIG. 2 is a sectional diagram that illustrates the schematic configuration of an objective optical system of Example 1 along with the paths of light rays that pass through the objective optical system.

The objective optical system of Example 1 is configured to satisfy all of Conditional Formulae (1) through (4). A cemented lens LS2 within a second lens group G2 of the objective optical system of Example 1 differs from that of an objective optical system of Example 2 to be described later, in that the cemented lens LS2 is formed by a fifth lens L5 having a positive refractive power and a sixth lens L6, which is a meniscus lens having a negative refractive power and a convex surface toward the image side, provided in this order from the object side.

Table 1 shows lens data of the objective optical system of Example 1. In the lens data shown in Table 1, surface numbers Si (i=1, 2, 3, . . . ) are surface numbers that sequentially increase from the object side to the image side, with the surface provided most toward the object side designated as 1. Note that the lens data also include surface numbers of an aperture stop St, optical elements LL (for example, an optical path converting prism, a filter, etc.) that do not have any power, and an imaging surface on which the optical image Im is focused.

The symbol Ri in Table 1 indicates the radii of curvature of $i^{th}$ (i=1, 2, 3, . . . ) surfaces. The symbol Di indicates the distances between $i^{th}$ surfaces and $i+1^{st}$ surfaces along the optical axis Z1. The numbers of the values indicated for the symbol Ri and the symbol Si correspond to the numbers of the symbol Si (i=1, 2, 3, . . . ) that indicate lens surfaces, the aperture stop, etc. Note that in Table 1, the units of measurement for the radii of curvature and the distances among surfaces are mm. The signs of the radii of curvature are positive in the case that surfaces are convex toward the object side, and negative in the case that surfaces are convex toward the image side.

The symbol Ndj in Table 1 indicates the refractive indices of $j^{th}$ (j=1, 2, 3, . . . ) optical elements with respect to the d line (wavelength: 587.6 nm), and vdj indicates the Abbe's numbers of $j^{th}$ optical elements (optical members) with respect to the d line. j is a number that sequentially increases from the object side to the image side, with the optical element most toward the object side designated as 1.

Note that it is possible for optical systems such as that described above to be proportionately enlarged or proportionately reduced and utilized. Therefore, objective optical systems in which the entirety of the aforementioned lens data is proportionately enlarged or proportionately reduced may be Examples of the present invention as well.

TABLE 1

Example 1: Lens Data

| Surface Number (i) | Radius of Curvature (Ri) | Distance (Di) | Ndj | vdj |
|---|---|---|---|---|
| 1 | 4.9998 | 0.25 | 1.88300 | 40.80 |
| 2 | 0.5800 | 0.44 | | |
| 3 | ∞ | 0.75 | 1.72825 | 28.50 |
| 4 | −0.6452 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −0.9258 | 0.12 | | |
| 9 | 2.4390 | 0.76 | 1.62041 | 60.30 |
| 10 | −0.7143 | 0.27 | 2.10205 | 16.80 |
| 11 | −1.1886 | 0.37 | | |
| 12 | ∞ | 2.00 | 1.55920 | 53.90 |
| 13 | ∞ | 0.15 | 1.51633 | 64.10 |
| 14 | ∞ | 0.00 | | |

Figure 10:
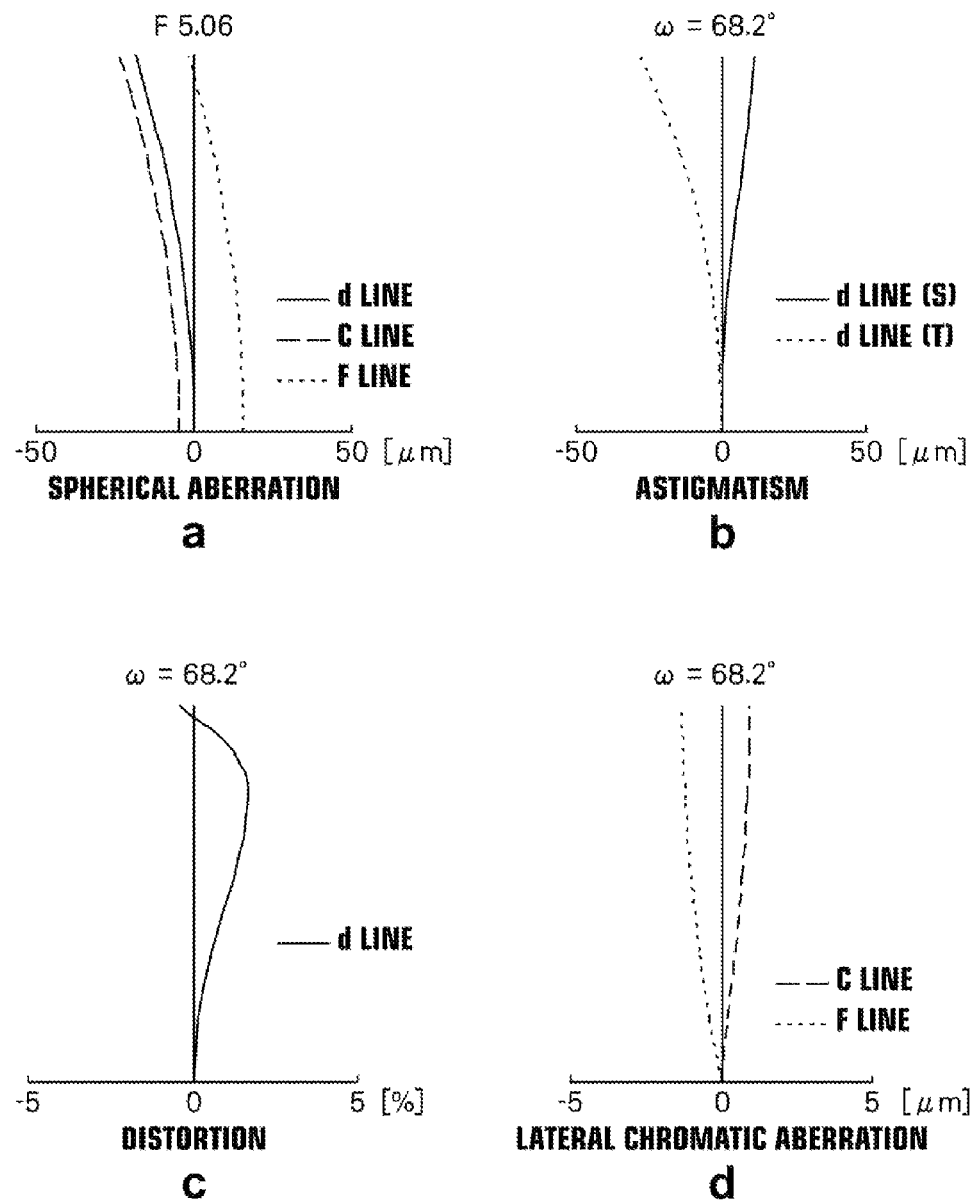
FIG. 10 is collection of diagrams that illustrate aberrations of the objective optical system of Example 1.

FIG. 10 is a collection of diagrams that illustrate aberrations regarding the objective optical system of Example 1. a of FIG. 10 illustrates spherical aberration, b of FIG. 10 illustrates astigmatism, c of FIG. 10 illustrates distortion, and d of FIG. 10 illustrates lateral chromatic aberration.

Note that in the diagram that illustrates astigmatism, the solid line indicates aberration in a sagittal direction, and the broken line indicates aberration in a tangential direction. In addition, "F5.06" shown above the diagram that illustrates spherical aberration indicates that the F number is 5.06. "ω=68.2°" shown above the diagrams that illustrate other aberrations indicate that the half angle of view is 68.2°.

Further, values of the objective optical system of Example 1 that correspond to the equations and variables in each of the conditional formulae described above are shown in Table 9. The values of the equations and variables can be derived from the lens data shown in Table 1 and the like. Note that the focal lengths of the lenses corresponding to the variables within the equations, and the focal lengths of combinations of a plurality of lenses (combined focal lengths) are distinguished as positive and negative.

Table 9 also shows values of objective optical systems of Examples 2 through 8 to be described later that correspond to the equations and variables in each of the conditional formulae described above.

The manners in which FIG. 2 that illustrates the configuration, FIG. 10 that illustrates the aberrations, Table 1 that shows the lens data, and Table 9 related to the conditional formulae of the objective optical system of Example 1 are to be interpreted are the same as those for the figures and tables related to Examples 2 through 8 to be described later. Therefore, descriptions thereof will be omitted with respect to the Examples to be described later.

Example 2

FIG. 3 is a sectional diagram that illustrates the schematic configuration of an objective optical system of Example 2 along with the paths of light rays that pass through the objective optical system.

The objective optical system of Example 2 is configured to satisfy all of Conditional Formulae (1) through (4). A cemented lens LS2 within a second lens group G2 of the objective optical system of Example 2 differs from that of the objective optical system of Example 1, in that the cemented lens LS2 is formed by a fifth lens L5 having a negative refractive power and a sixth lens L6, which is a lens having a positive refractive power and a convex surface toward the image side, provided in this order from the object side.

Figure 11:
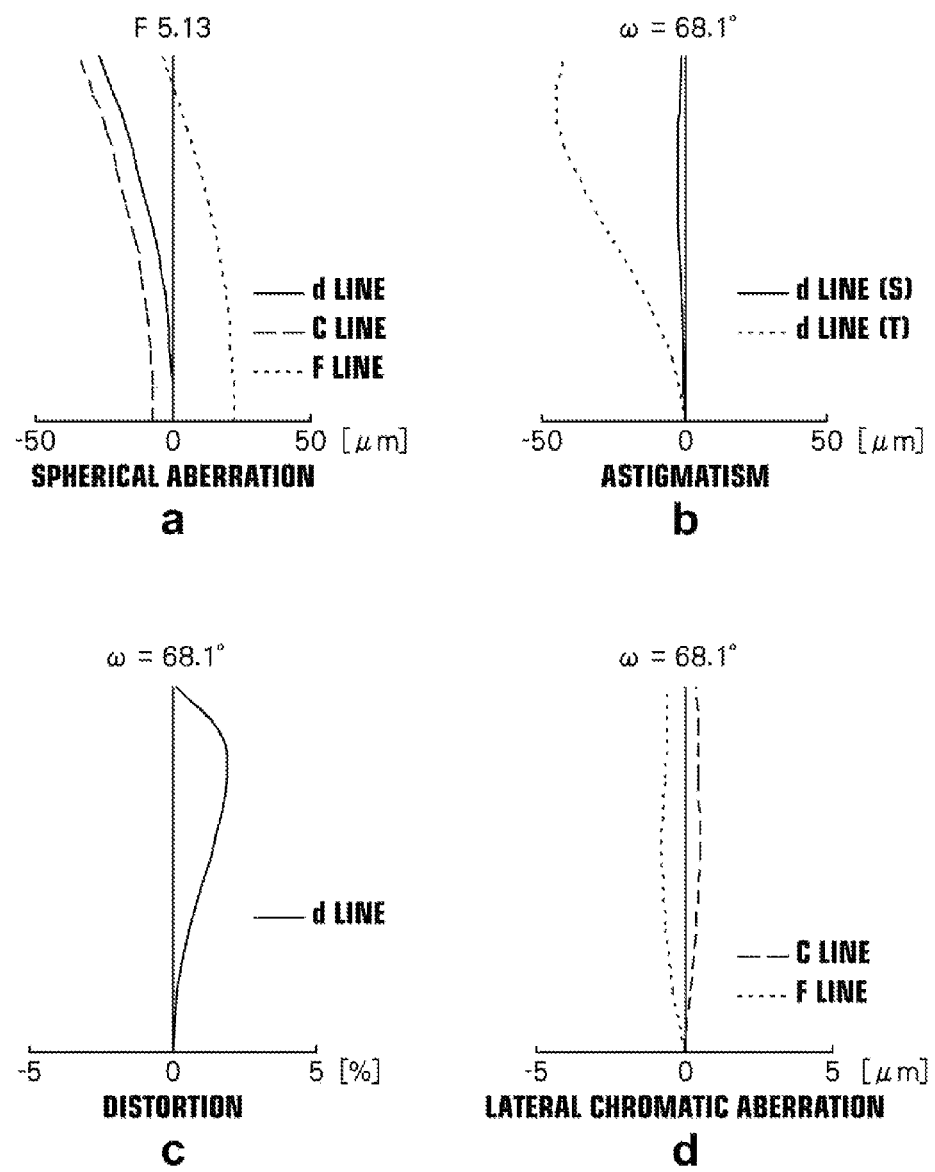
FIG. 11 is collection of diagrams that illustrate aberrations of the objective optical system of Example 2.

FIG. 11 is a collection of diagrams that illustrate aberrations of the objective optical system of Example 2.

Table 2 below shows lens data of the objective optical system of Example 2.

TABLE 2

Example 2: Lens Data

| Surface Number (i) | Radius of Curvature (Ri) | Distance (Di) | Ndj | vdj |
|---|---|---|---|---|
| 1 | 5.3203 | 0.25 | 1.88300 | 40.80 |
| 2 | 0.5800 | 0.48 | | |
| 3 | ∞ | 0.75 | 1.72825 | 28.50 |
| 4 | −0.7127 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −1.2431 | 0.10 | | |
| 9 | 1.6189 | 0.25 | 1.95906 | 17.50 |
| 10 | 0.8124 | 0.82 | 1.62041 | 60.30 |
| 11 | −1.3016 | 0.28 | | |

TABLE 2-continued

Example 2: Lens Data

| Surface Number (i) | Radius of Curvature (Ri) | Distance (Di) | Ndj | vdj |
|---|---|---|---|---|
| 12 | ∞ | 2.00 | 1.55920 | 53.90 |
| 13 | ∞ | 0.30 | 1.51633 | 64.10 |
| 14 | ∞ | 0.00 | | |

Example 3

FIG. 4 is a sectional diagram that illustrates the schematic configuration of an objective optical system of Example 3 along with the paths of light rays that pass through the objective optical system.

The objective optical system of Example 3 is configured to satisfy all of Conditional Formulae (1) through (4). A cemented lens LS2 within a second lens group G2 of the objective optical system of Example 3 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

FIG. 12 is a collection of diagrams that illustrate aberrations of the objective optical system of Example 3.

Table 3 below shows lens data of the objective optical system of Example 3.

TABLE 3

Example 3: Lens Data

| Surface Number (i) | Radius of Curvature (Ri) | Distance (Di) | Ndj | vdj |
|---|---|---|---|---|
| 1 | 5.2535 | 0.25 | 1.88300 | 40.80 |
| 2 | 0.5800 | 0.44 | | |
| 3 | ∞ | 0.75 | 1.72825 | 28.50 |
| 4 | −0.6452 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −0.9202 | 0.10 | | |
| 9 | 2.3148 | 0.78 | 1.62041 | 60.30 |
| 10 | −0.7407 | 0.27 | 2.10205 | 16.80 |
| 11 | −1.2428 | 0.37 | | |
| 12 | ∞ | 2.00 | 1.55920 | 53.90 |
| 13 | ∞ | 0.15 | 1.51633 | 64.10 |
| 14 | ∞ | 0.00 | | |

Example 4

FIG. 5 is a sectional diagram that illustrates the schematic configuration of an objective optical system of Example 4 along with the paths of light rays that pass through the objective optical system.

The objective optical system of Example 4 is configured to satisfy all of Conditional Formulae (1) through (4). A cemented lens LS2 within a second lens group G2 of the objective optical system of Example 4 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

FIG. 13 is a collection of diagrams that illustrate aberrations of the objective optical system of Example 4.

Table 4 below shows lens data of the objective optical system of Example 4.

TABLE 4

Example 4: Lens Data

| Surface Number (i) | Radius of Curvature (Ri) | Distance (Di) | Ndj | vdj |
|---|---|---|---|---|
| 1 | 4.9998 | 0.25 | 1.88300 | 40.80 |
| 2 | 0.5800 | 0.44 | | |
| 3 | ∞ | 0.75 | 1.72825 | 28.50 |
| 4 | −0.6452 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −0.9127 | 0.10 | | |
| 9 | 2.3104 | 0.78 | 1.62041 | 60.30 |
| 10 | −0.7407 | 0.27 | 2.15400 | 17.20 |
| 11 | −1.2209 | 0.36 | | |
| 12 | ∞ | 2.00 | 1.55920 | 53.90 |
| 13 | ∞ | 0.15 | 1.51633 | 64.10 |
| 14 | ∞ | 0.00 | | |

Example 5

FIG. 6 is a sectional diagram that illustrates the schematic configuration of an objective optical system of Example 5 along with the paths of light rays that pass through the objective optical system.

The objective optical system of Example 5 is configured to satisfy all of Conditional Formulae (1) through (4). A cemented lens LS2 within a second lens group G2 of the objective optical system of Example 5 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

Figure 14:
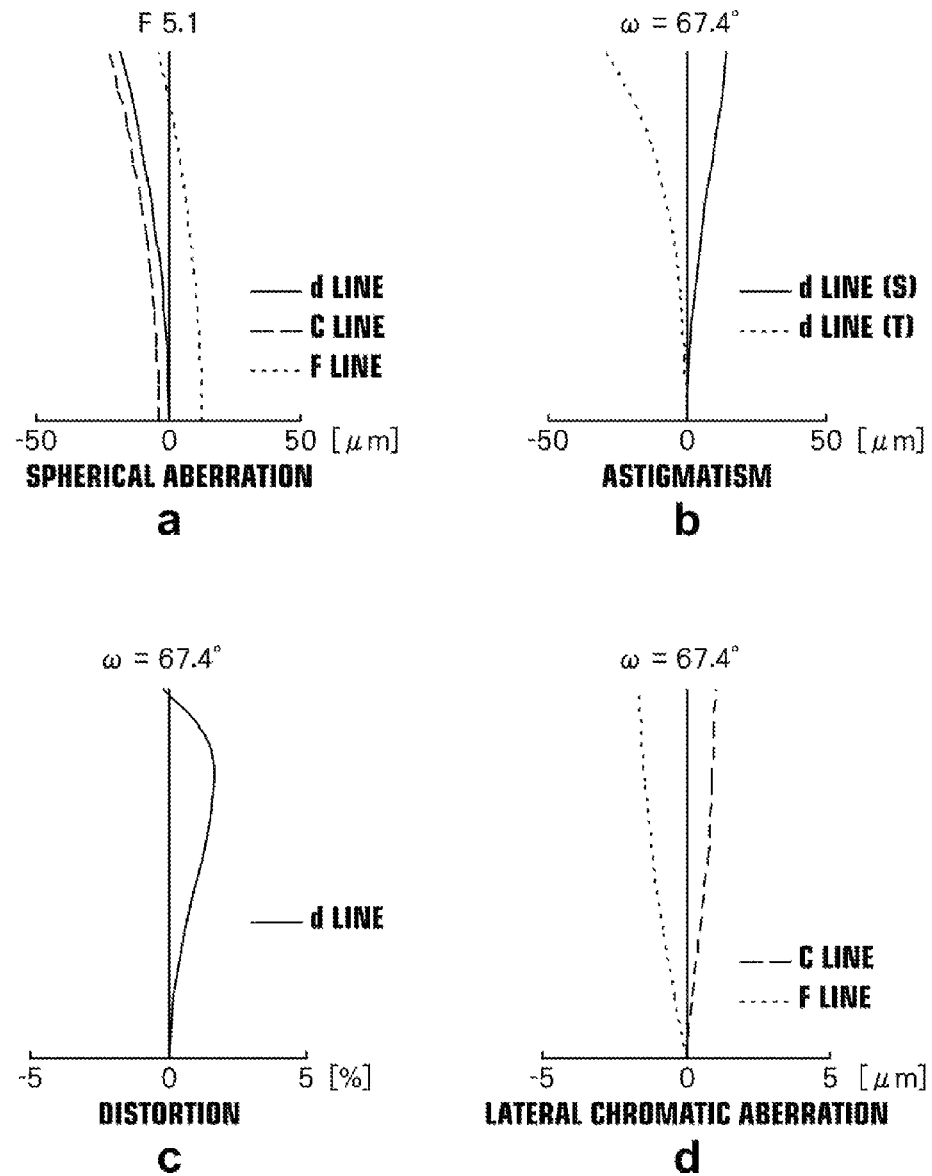
FIG. 14 is collection of diagrams that illustrate aberrations of the objective optical system of Example 5.

FIG. 14 is a collection of diagrams that illustrate aberrations of the objective optical system of Example 5.

Table 5 below shows lens data of the objective optical system of Example 5.

TABLE 5

Example 5: Lens Data

| Surface Number (i) | Radius of Curvature (Ri) | Distance (Di) | Ndj | vdj |
|---|---|---|---|---|
| 1 | 4.9998 | 0.25 | 1.88300 | 40.80 |
| 2 | 0.5800 | 0.44 | | |
| 3 | ∞ | 0.75 | 1.72825 | 28.50 |
| 4 | −0.6452 | 0.25 | 1.88300 | 40.80 |
| 5 | ∞ | 0.04 | | |
| 6 (Aperture Stop) | ∞ | 0.00 | | |
| 7 | ∞ | 0.75 | 1.51633 | 64.10 |
| 8 | −0.9350 | 0.10 | | |
| 9 | 2.3735 | 0.78 | 1.62041 | 60.30 |
| 10 | −0.7407 | 0.27 | 1.94595 | 18.00 |
| 11 | −1.3308 | 0.34 | | |
| 12 | ∞ | 2.00 | 1.55920 | 53.90 |
| 13 | ∞ | 0.15 | 1.51633 | 64.10 |
| 14 | ∞ | 0.00 | | |

Example 6

FIG. 7 is a sectional diagram that illustrates the schematic configuration of an objective optical system of Example 6 along with the paths of light rays that pass through the objective optical system.

The objective optical system of Example 6 is configured to satisfy all of Conditional Formulae (1) through (4). A cemented lens LS2 within a second lens group G2 of the objective optical system of Example 6 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

FIG. 15 is a collection of diagrams that illustrate aberrations of the objective optical system of Example 6.

Table 6 below shows lens data of the objective optical system of Example 6.

TABLE 6

Example 6: Lens Data

| Surface Number (i) | Radius of Curvature (Ri) | Distance (Di) | Ndj | vdj |
|---|---|---|---|---|
| 1 | 4.9998 | 0.25 | 1.88300 | 40.80 |
| 2 | 0.5800 | 0.44 | | |
| 3 | ∞ | 0.75 | 1.72825 | 28.50 |
| 4 | −0.6452 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −0.9258 | 0.12 | | |
| 9 | 2.4390 | 0.76 | 1.62041 | 60.30 |
| 10 | −0.7143 | 0.27 | 2.10205 | 16.80 |
| 11 | −1.1886 | 0.37 | | |
| 12 | ∞ | 2.00 | 1.55920 | 53.90 |
| 13 | ∞ | 0.15 | 1.51633 | 64.10 |
| 14 | ∞ | 0.00 | | |

Example 7

FIG. 8 is a sectional diagram that illustrates the schematic configuration of an objective optical system of Example 7 along with the paths of light rays that pass through the objective optical system.

The objective optical system of Example 7 is configured to satisfy all of Conditional Formulae (1) through (4). A cemented lens LS2 within a second lens group G2 of the objective optical system of Example 7 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

FIG. 16 is a collection of diagrams that illustrate aberrations of the objective optical system of Example 7.

Table 7 below shows lens data of the objective optical system of Example 7.

TABLE 7

Example 7: Lens Data

| Surface Number (i) | Radius of Curvature (Ri) | Distance (Di) | Ndj | vdj |
|---|---|---|---|---|
| 1 | 5.0988 | 0.25 | 1.88300 | 40.80 |
| 2 | 0.5800 | 0.44 | | |
| 3 | ∞ | 0.75 | 1.72825 | 28.50 |
| 4 | −0.6494 | 0.25 | 1.88300 | 40.80 |
| 5 | ∞ | 0.04 | | |
| 6 (Aperture Stop) | ∞ | 0.00 | | |
| 7 | ∞ | 0.73 | 1.51633 | 64.10 |
| 8 | −0.9072 | 0.10 | | |

TABLE 7-continued

Example 7: Lens Data

| Surface Number (i) | Radius of Curvature (Ri) | Distance (Di) | Ndj | vdj |
|---|---|---|---|---|
| 9 | 2.4390 | 0.78 | 1.62041 | 60.30 |
| 10 | −0.7407 | 0.27 | 2.10205 | 16.80 |
| 11 | −1.2342 | 0.36 | | |
| 12 | ∞ | 2.00 | 1.55920 | 53.90 |
| 13 | ∞ | 0.15 | 1.51633 | 64.10 |
| 14 | ∞ | 0.00 | | |

Example 8

FIG. 9 is a sectional diagram that illustrates the schematic configuration of an objective optical system of Example 8 along with the paths of light rays that pass through the objective optical system.

The objective optical system of Example 8 is configured to satisfy all of Conditional Formulae (1) through (4). A cemented lens LS2 within a second lens group G2 of the objective optical system of Example 8 is the same as that of Example 1. That is, the cemented lens LS2 is formed by a fifth lens L5 having a positive refractive power and a sixth lens L6, which is a meniscus lens having a negative refractive power and a convex surface toward the image side, provided in this order from the object side.

Figure 17:
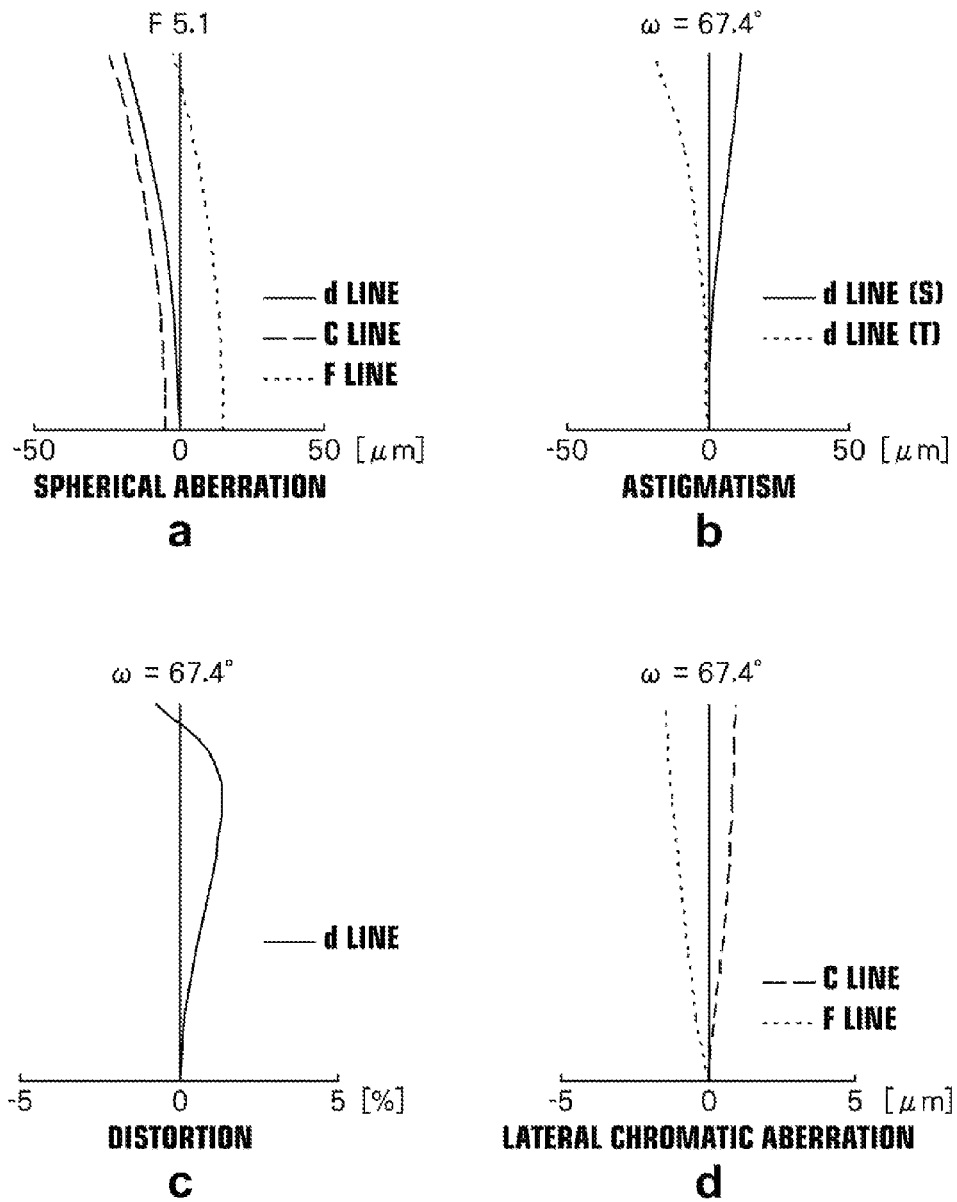
FIG. 17 is collection of diagrams that illustrate aberrations of the objective optical system of Example 8.

FIG. 17 is a collection of diagrams that illustrate aberrations of the objective optical system of Example 8.

Table 8 below shows lens data of the objective optical system of Example 8.

TABLE 8

Example 8: Lens Data

| Surface Number (i) | Radius of Curvature (Ri) | Distance (Di) | Ndj | vdj |
|---|---|---|---|---|
| 1 | 4.9998 | 0.25 | 1.88300 | 40.80 |
| 2 | 0.5556 | 0.44 | | |
| 3 | 8.4585 | 0.75 | 1.72825 | 28.50 |
| 4 | −0.6565 | 0.25 | 1.88300 | 40.80 |
| 5 | 5.6421 | 0.04 | | |
| 6 (Aperture Stop) | ∞ | 0.00 | | |
| 7 | 3.0775 | 0.73 | 1.51633 | 64.10 |
| 8 | −0.9789 | 0.12 | | |
| 9 | 2.4390 | 0.76 | 1.62041 | 60.30 |
| 10 | −0.7143 | 0.27 | 2.10205 | 16.80 |
| 11 | −1.1813 | 0.37 | | |
| 12 | ∞ | 2.00 | 1.55920 | 53.90 |
| 13 | ∞ | 0.15 | 1.51633 | 64.10 |
| 14 | ∞ | 0.00 | | |

As described previously, Table 9 shows values related to each of the conditional formulae.

TABLE 9

| Conditional Formula | Equation within Conditional Formula | Values of Equations in Conditional Formula | | | | | | | |
|---|---|---|---|---|---|---|---|---|---|
| | | Example 1 | Example 2 | Example 3 | Example 4 | Example 5 | Example 6 | Example 7 | Example 8 |
| (1) | f123/f | −0.94 | −0.97 | −0.94 | −0.94 | −0.95 | −0.95 | −0.94 | −0.81 |
| (2) | f456/f | 1.94 | 1.98 | 1.92 | 1.92 | 1.92 | 1.95 | 1.92 | 1.88 |
| (3) | f1/f | −1.31 | −1.31 | −1.3 | −1.31 | −1.31 | −1.32 | −1.31 | −1.24 |
| (4) | f2 − 6/f | 1.99 | 2.03 | 1.98 | 1.97 | 1.97 | 2 | 1.98 | 2.05 |

The present invention has been described with reference to the embodiments and Examples thereof. However, the present invention is not limited to the embodiments and Examples described above, and various modifications are possible. For example, the values of the radii of curvature of each lens component, the distances among surfaces, the refractive indices, the Abbe's numbers, etc., are not limited to the numerical values indicated in connection with the Examples, and may be other values.

What is claimed is:

1. An objective optical system, comprising:
a first lens group having a negative refractive power;
an aperture stop; and
a second lens group having a positive refractive power, provided in this order from an object side;
the first lens group comprising a negative single lens and a cemented lens formed by cementing a positive lens and a negative lens together, provided in this order from the object side;
the second lens group comprising a positive single lens and a cemented lens formed by cementing a positive lens and a negative lens together, provided in this order from the object side;
the cemented lens within the first lens group being formed by a positive lens having a convex surface toward the image side and a negative lens, provided in this order from the object side; and
the objective optical system simultaneously satisfying Conditional Formulae (1) and (2) below:

$$-1.5 < f123/f < -0.5 \quad (1)$$

$$1.8 < f456/f < 2.1 \quad (2)$$

wherein f is the combined focal length of the entire lens system, f123 is the combined focal length of the first lens group, and f456 is the combined focal length of the second lens group.

2. An objective optical system as defined in claim 1 that satisfies Conditional Formula (3) below:

$$f1/f < -1.1 \quad (3)$$

wherein f1 is the focal length of the lens provided most toward the object side, and f is the focal length of the entire lens system.

3. An objective optical system as defined in claim 1 that satisfies Conditional Formula (4) below:

$$1.92 < f2-6/f < 3 \quad (4)$$

wherein f2−6 is the combined focal length of the lenses other than the lens provided most toward the object side, and f is the focal length of the entire lens system.

4. An objective optical system as defined in claim 1 that satisfies Conditional Formula (1a) below:

$$-1.4 < f123/f < -0.6 \tag{1a}$$

5. An objective optical system as defined in claim 1 that satisfies Conditional Formula (2a) below:

$$1.84 < f456/f < 2.1 \tag{2a}$$

6. An objective optical system as defined in claim 1 that satisfies Conditional Formula (1b) below:

$$-1.3 < f123/f < -0.7 \tag{1b}$$

7. An objective optical system as defined in claim 1 that satisfies Conditional Formula (2b) below:

$$1.86 < f456/f < 2.0 \tag{2b}$$

8. An objective optical system as defined in claim 1 that satisfies Conditional Formula (3a) below:

$$-1.5 < f1/f < -1.1 \tag{3a}$$

9. An objective optical system as defined in claim 1 that satisfies Conditional Formula (3b) below:

$$-1.4 < f1/f < -1.2 \tag{3b}$$

10. An objective optical system as defined in claim 1 that satisfies Conditional Formula (4a) below:

$$1.92 < f2-6/f < 2.5 \tag{4a}$$

11. An objective optical system as defined in claim 1 that satisfies Conditional Formula (4b) below:

$$1.92 < f2-6/f < 2.2 \tag{4b}$$

12. An objective optical system as defined in claim 1 which is employed as an objective optical system for an endoscope.

13. An endoscope equipped with an objective optical system as defined in claim 1.

14. An objective optical system as defined in claim 1, wherein:
the cemented lens within the second lens group is formed by a positive lens and a negative meniscus lens having a convex surface toward the image side, provided in this order from the object side.

15. An objective optical system as defined in claim 14 that satisfies Conditional Formula (3) below:

$$f1/f < -1.1 \tag{3}$$

wherein f1 is the focal length of the lens provided most toward the object side, and f is the focal length of the entire lens system.

16. An objective optical system as defined in claim 14 that satisfies Conditional Formula (4) below:

$$1.92 < f2-6/f < 3 \tag{4}$$

wherein f2-6 is the combined focal length of the lenses other than the lens provided most toward the object side, and f is the focal length of the entire lens system.

17. An objective optical system as defined in claim 1, wherein:
the cemented lens within the second lens group is formed by a negative lens and a positive lens having a convex surface toward the image side, provided in this order from the object side.

18. An objective optical system as defined in claim 17 that satisfies Conditional Formula (3) below:

$$f1/f < -1.1 \tag{3}$$

wherein f1 is the focal length of the lens provided most toward the object side, and f is the focal length of the entire lens system.

19. An objective optical system as defined in claim 17 that satisfies Conditional Formula (4) below:

$$1.92 < f2-6/f < 3 \tag{4}$$

wherein f2-6 is the combined focal length of the lenses other than the lens provided most toward the object side, and f is the focal length of the entire lens system.

* * * * *